United States Patent
Schorgl et al.

(10) Patent No.: US 6,808,504 B2
(45) Date of Patent: Oct. 26, 2004

(54) MULTI-LUMEN IMPLANT

(75) Inventors: John Schorgl, Eden Prairie, MN (US); David Mowry, Waconia, MN (US); Rob Kohler, Lake Elmo, MN (US)

(73) Assignee: Percardia, Inc., Merrimack, NH (US)

( * ) Notice: Subject to any disclaimer, the term of this patent is extended or adjusted under 35 U.S.C. 154(b) by 142 days.

(21) Appl. No.: 09/971,354

(22) Filed: Oct. 4, 2001

(65) Prior Publication Data

US 2003/0069587 A1 Apr. 10, 2003

(51) Int. Cl.⁷ .......................... A61M 5/00; A61F 2/06
(52) U.S. Cl. .................... 604/8; 623/1.13; 623/1.27
(58) Field of Search ................. 604/7–9, 6.16, 604/48; 600/16–18; 623/1.16, 1.27, 1.32, 1.13

(56) References Cited

U.S. PATENT DOCUMENTS

| | | | | |
|---|---|---|---|---|
| 4,995,857 A | * | 2/1991 | Arnold | 600/16 |
| 5,287,861 A | | 2/1994 | Wilk | |
| 5,409,019 A | | 4/1995 | Wilk | |
| 5,655,548 A | * | 8/1997 | Nelson et al. | 128/898 |
| 5,755,682 A | | 5/1998 | Knudson et al. | |
| 5,824,071 A | * | 10/1998 | Nelson et al. | 606/194 |
| 5,908,029 A | | 6/1999 | Knudson et al. | |
| 5,921,952 A | * | 7/1999 | Desmond et al. | 604/8 |
| 5,944,019 A | | 8/1999 | Knudson et al. | |
| 5,984,956 A | | 11/1999 | Tweden et al. | |
| 6,029,672 A | | 2/2000 | Vanney et al. | |
| 6,044,845 A | * | 4/2000 | Lewis | 128/898 |
| 6,053,942 A | | 4/2000 | Eno et al. | |
| 6,076,529 A | | 6/2000 | Vanney et al. | |
| 6,093,166 A | | 7/2000 | Knudson et al. | |
| 6,102,941 A | | 8/2000 | Tweden et al. | |
| 6,113,630 A | | 9/2000 | Vanney et al. | |
| 6,113,823 A | | 9/2000 | Eno | |
| 6,123,682 A | | 9/2000 | Knudson et al. | |
| 6,139,541 A | | 10/2000 | Vanney et al. | |
| 6,182,668 B1 | | 2/2001 | Tweden et al. | |
| 6,193,726 B1 | | 2/2001 | Vanney | |
| 6,197,050 B1 | | 3/2001 | Eno et al. | |
| 6,214,041 B1 | | 4/2001 | Tweden et al. | |
| 6,223,752 B1 | | 5/2001 | Vanney et al. | |
| 6,237,607 B1 | | 5/2001 | Vanney et al. | |
| 6,250,305 B1 | | 6/2001 | Tweden | |
| 6,253,768 B1 | * | 7/2001 | Wilk | 128/898 |

* cited by examiner

*Primary Examiner*—Angela D. Sykes
*Assistant Examiner*—Leslie R Deak
(74) *Attorney, Agent, or Firm*—Finnegan, Henderson, Farabow, Garrett & Dunner, L.L.P.

(57) ABSTRACT

An implant for use in direct left ventricle to coronary vessel revascularization is disclosed. The implant includes a sleeve sized to pass through a heart wall. The sleeve is sufficiently rigid to remain open during contraction of the heart. The implant also includes a plurality of conduits at least partially mounted in the sleeve.

14 Claims, 7 Drawing Sheets

MULTI-LUMEN IMPLANT

FIELD OF THE INVENTION

The present invention pertains to an implant for passing blood directly between a chamber of the heart and a coronary vessel.

BACKGROUND

The placing of artificial shunts or other durable passageways in the heart wall to connect heart chambers containing oxygenated blood with coronary arteries also is known. These devices and the techniques for placing them in the heart are described in detail in U.S. Pat. No. 5,944,019, issued Aug. 31, 1999, which is hereby incorporated by reference. Such implants typically are placed in the wall of the heart to allow oxygenated blood to flow into a partially or completely occluded coronary artery as an alternative to more traditional or conventional vein graft coronary arterial bypass procedures.

SUMMARY OF THE INVENTION

According to an embodiment of the present invention, a transmyocardial implant is disclosed for establishing a blood flow path through a myocardium between a heart chamber and more than one coronary vessel. The implant includes a rigid housing sized to be inserted into and retained within the myocardium. The rigid conduit is sufficiently rigid to withstand collapse in response to contraction forces of the myocardium. Additionally, the implant includes a plurality of conduits, each conduit having a first end secured in the rigid housing and a second end sized to be secured to a coronary vessel. The conduits are blood compatible. The rigid housing and the conduits define blood flow paths from the heart chamber to more than one coronary vessel.

A variety of additional advantages of the invention will be set forth in the description which follows, and will be apparent from the description. It is to be understood that both the foregoing material and the following detailed description are exemplary and explanatory only, and are not restrictive of the invention as claimed.

BRIEF DESCRIPTION OF THE DRAWINGS

The accompanying drawings, which are incorporated in and constitute a part of this specification, illustrate several aspects of the invention and together with the description, serve to explain the principles of the invention. A brief description of the drawings is as follows.

DETAILED DESCRIPTION

Reference will now be made in detail to exemplary aspects of the present invention that are illustrated in the accompanying drawings. The same reference numbers will be used throughout the drawings to refer to the same or like parts. It should be noted that throughout the description, the terms "including" and "having" are used synonymously with "comprising".

Figure 1:
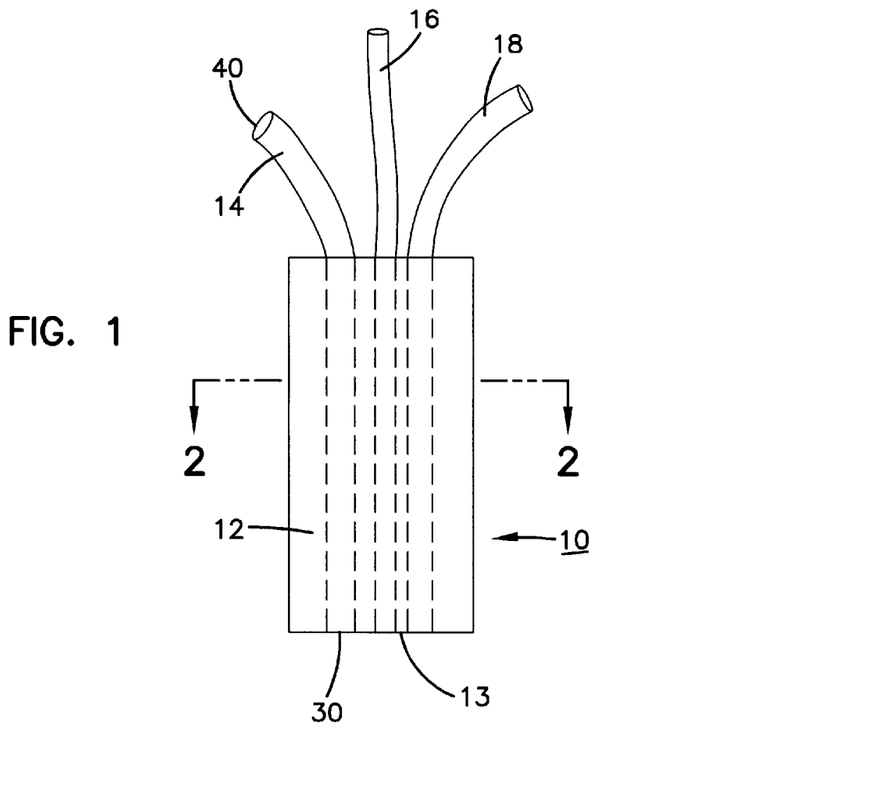
FIG. 1 is a perspective view of an implant according to an embodiment of the present invention.
Figure 2:
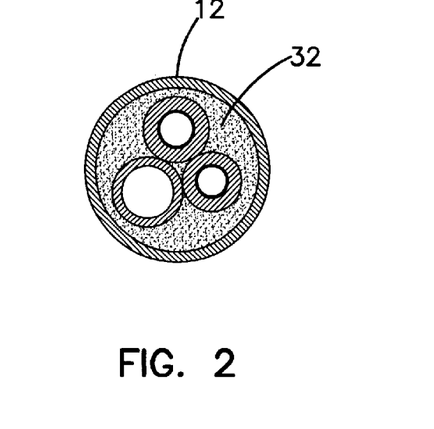
FIG. 2 is a cross-sectional end view of the implant shown in FIG. 1 taken along section line 2—2.
Figure 3:
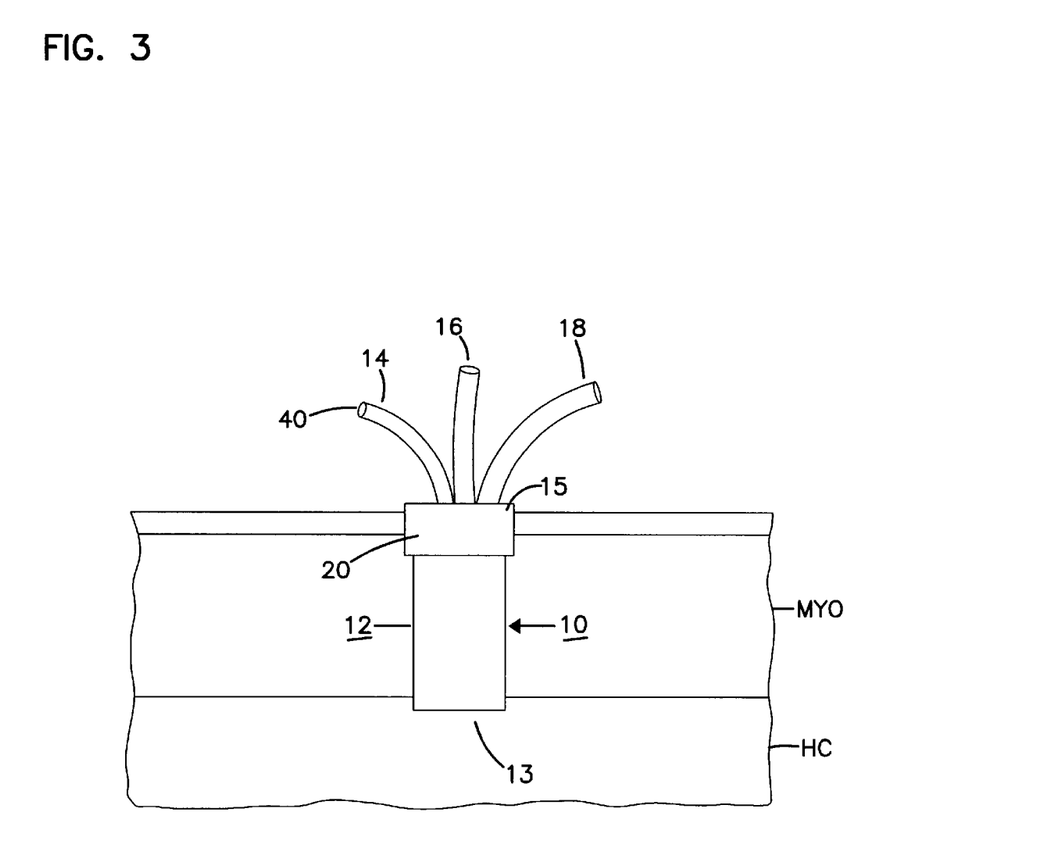
FIG. 3 is a side sectional view of an implant according to an embodiment of the present invention shown in place in a human heart wall.

FIGS. 1–3 show an implant 10 including a hollow, rigid housing 12 and a plurality of flexible conduits 14, 16, and 18. The housing 12 may be formed of titanium or another rigid biocompatible material such as nickel-titanium alloy or pyrolytic carbon or may be titanium or another material that is coated with pyrolytic carbon. The material of the housing 12 should be sufficiently rigid so as to withstand the contraction forces of the myocardium and maintain an open path through the myocardium during both systole and diastole. An end 13 of the housing 12 is sized to extend through the myocardium MYO of the human heart to project into the interior of a heart chamber HC (preferably, the left ventricle) by a distance of about 5 mm (see FIG. 3).

The housing 12 may be provided with tissue-growth inducing material 20 adjacent an upper end to immobilize the housing 12 within the myocardium MYO (shown in FIG. 3). The material 20 surrounds the exterior of the housing 12 and may be a polyester woven sleeve or sintered metal to define pores into which tissue growth from the myocardium MYO may occur.

The surgeon depending upon the nature of the procedure may select the number and size of the flexible conduits. The inner diameter of the flexible conduits preferably ranges from approximately 1 to 5 mm. Additionally, the length of the flexible conduits may vary. The length and inner diameter of the conduits need not be the same from conduit to conduit. In one non-limiting example, two flexible conduits may have an inner diameter of 1.5 mm while the third flexible conduit has an inner diameter of 4.0 mm. In another non-limiting example, the implant may include three flexible implants each having an inner diameter of 2.0 mm. In certain embodiments, a surgeon can cut the conduits to desired lengths.

The flexible conduits are preferably made from any suitable plastic material. Preferably, the flexible conduits are made from expanded polytetrafluorethylene. The use of ePTFE flexible conduits results in blood flowing through path being exposed only to ePTFE which is a material already used as a synthetic vessel with proven blood and tissue compatibility thereby reducing risk of thrombosis and encouraging endotheliazation.

Each flexible conduit has a first end 30 and a second end 40. The first end 30 of each flexible conduit is inserted through the interior of the housing 12 and secured. In one embodiment, the first ends of the flexible conduits are secured using a securing material 32, such as collagen or another suitable polymer. The ends 30 are secured by filling the voids formed between the flexible conduits with the securing material. The securing material may be injected or placed in the voids by another suitable means. Alternatively, the first ends 30 of the flexible conduits may be secured in the interior of the housing 12 by a forced fit.

The implant including the rigid housing 12 and plurality of flexible conduits is preferably placed in the myocardium MYO with the lower end of the housing protruding into the left ventricle HC, as shown in FIG. 3. The implant 10 thus defines open blood flow paths in blood flow communication with a heart chamber.

To bypass obstructions in more than one coronary vessel, ends 40 of the flexible conduits are attached to the coronary vessels in any suitable manner. For example, the ends 40 may be anastomosed to an artery with sutures (not shown) in an end-to-side anastomosis as is done in conventional coronary artery bypass procedures. Alternatively, the ends of the flexible conduits may be secured to the vessel using an end-end anastomosis. The ends 40 are secured to the appropriate vessels downstream from the obstructions. In certain embodiments, anastomosis devices such as those disclosed in U.S. Provisional Patent Application No. 60/304,208 and U.S. patent application Ser. No. 09/931,655, which are hereby incorporated by reference, can be used.

Figure 4:
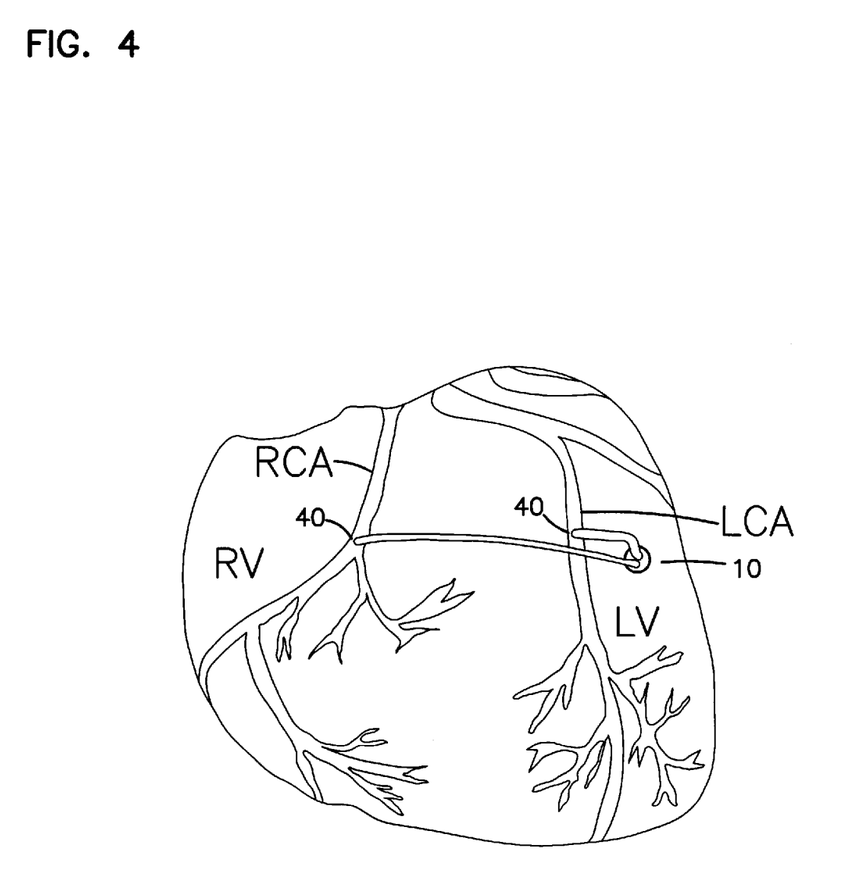
FIG. 4 is a plan view of an implant according to an embodiment of the present invention shown in place in a human heart establishing direct blood flow paths from a heart chamber to more than one coronary vessel.
Figure 5:
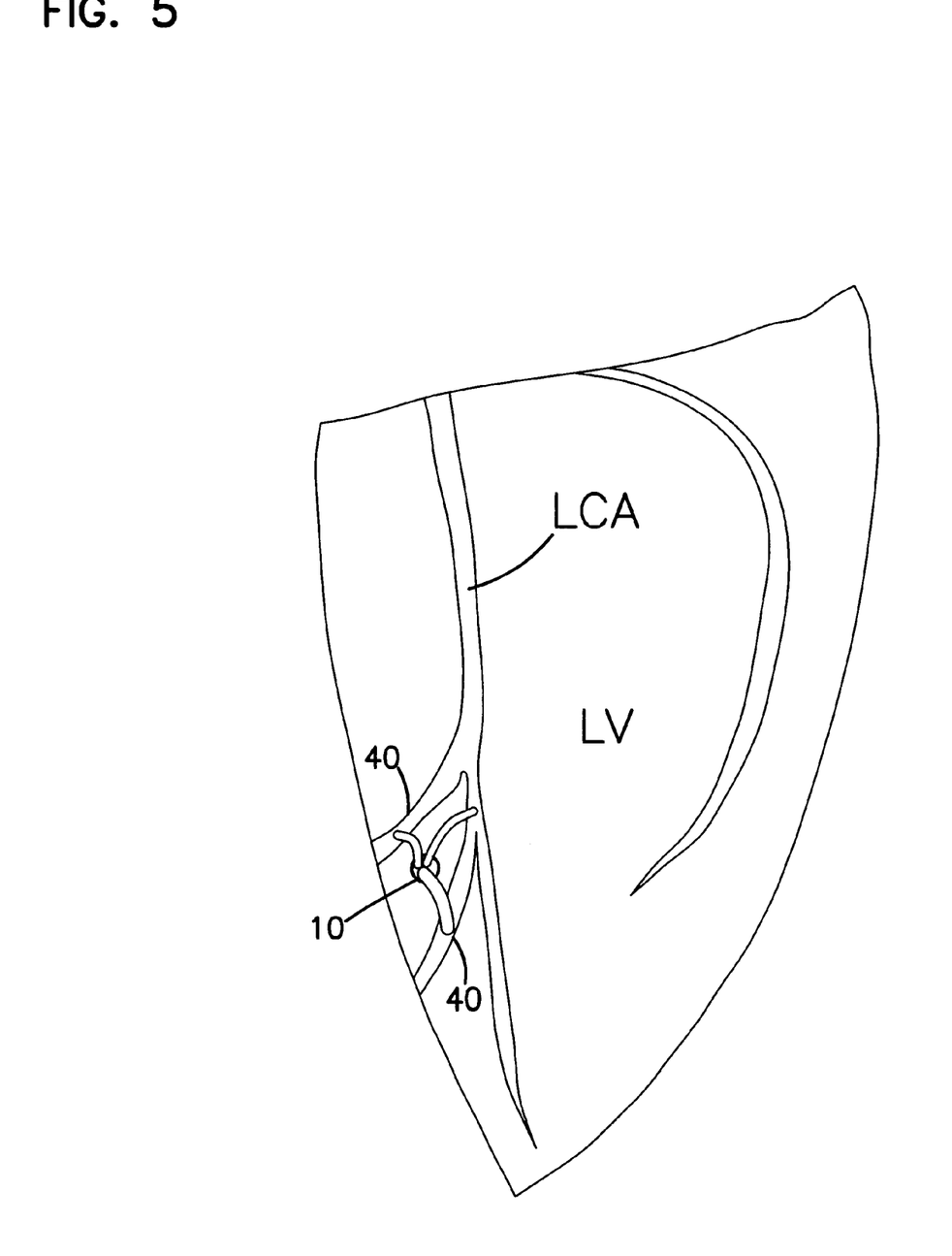
FIG. 5 is a plan view of an implant according to an embodiment of the present invention shown in place in a human heart establishing direct blood flow paths from a heart chamber to more than one coronary vessel.
Figure 6:
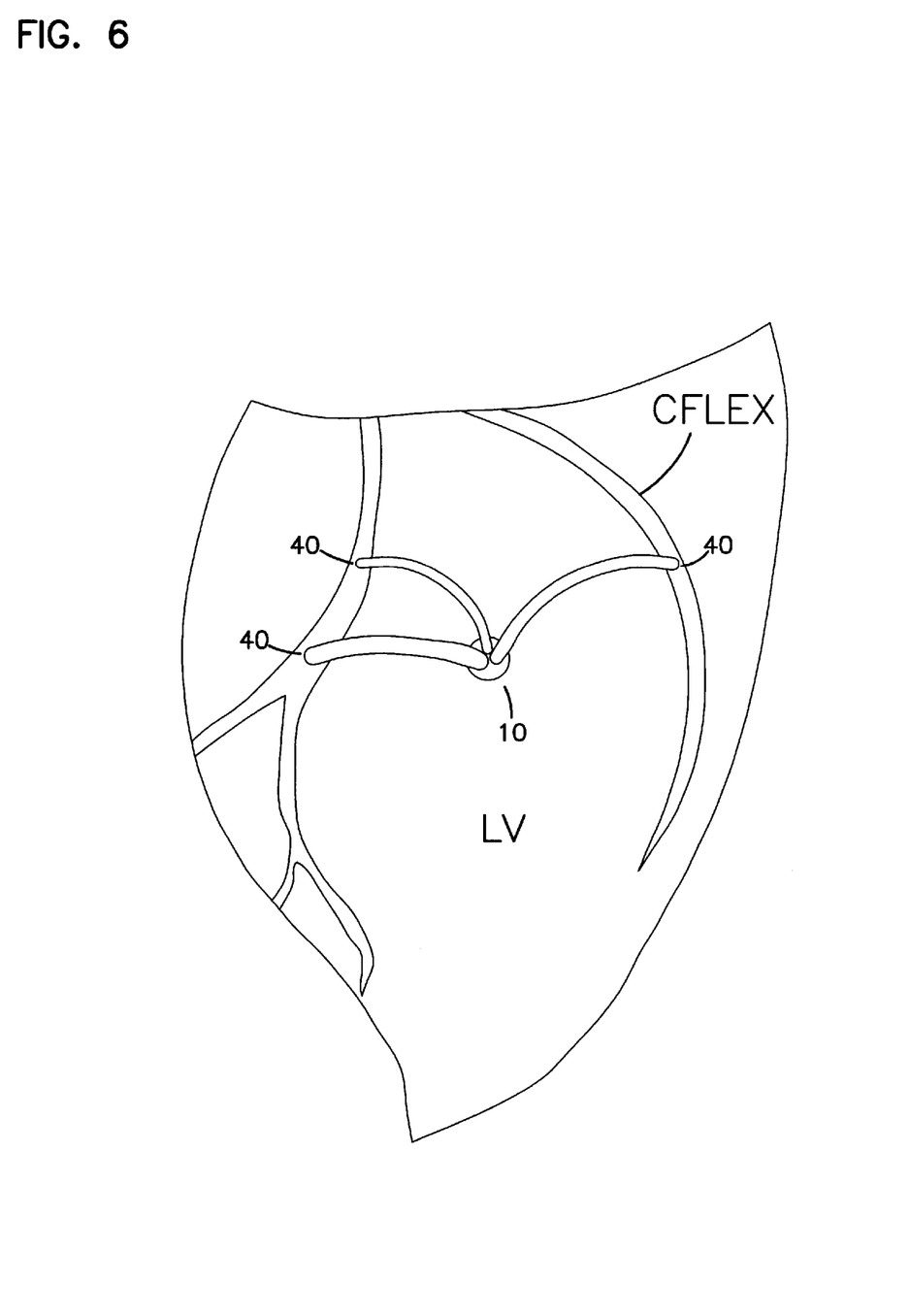
FIG. 6 is a plan view of an implant according to an embodiment of the present invention shown in place in a human heart establishing direct blood flow paths from a heart chamber to more than one coronary vessel.

For the purposes of this application, the term coronary vessels refers to the coronary arteries, coronary veins, and branches thereof. Ends 40 of the flexible conduits may be connected to a right coronary artery RCA and a left coronary artery LCA, as shown in FIG. 4; multiple sites on a single artery as shown in FIG. 5; or the ends may be connected to sites on the left coronary artery and on the circumflex branch as shown in FIG. 6. In addition to arteries, the ends 40 may be secured coronary veins such as in a retrograde profusion procedure.

With the above-described embodiments, the implant 10 permits revascularization from the left ventricle LV to more than one coronary vessel such as right and left coronary arteries RCA and LCA. The use of elongated, flexible conduits permits revascularization where the vessel CA is not necessarily in overlying relation to the chamber HC. For example, the implant 10 permits direct blood flow between the left ventricle HC and a vessel such as the right coronary artery RCA overlying the right ventricle as shown in FIG. 4.

Figure 7:
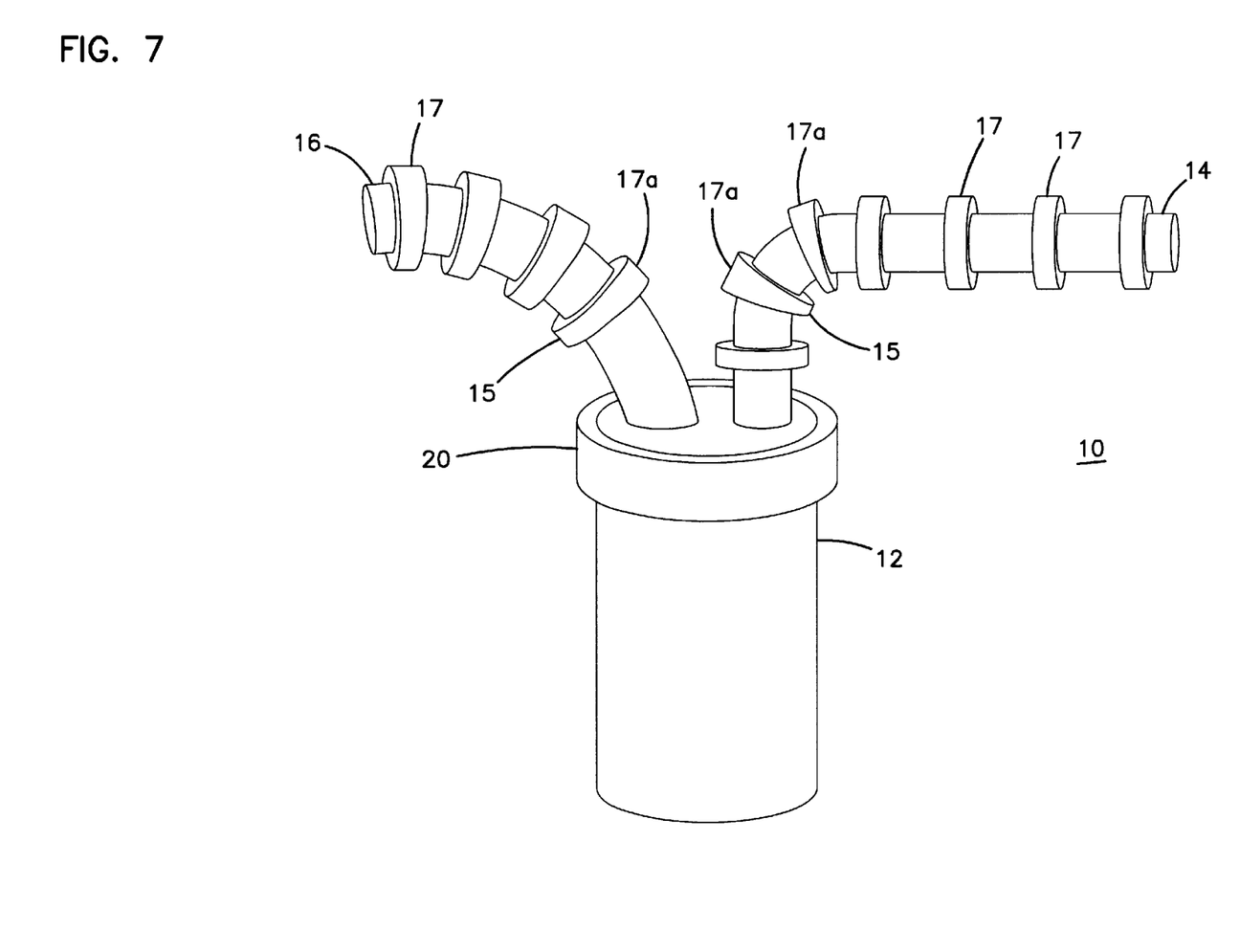
FIG. 7 is a perspective view of an implant according to an embodiment of the present invention.

In an alternative embodiment, a plurality of discrete rigid rings 17 (shown in FIG. 7) may be provided along the length of the flexible conduit not located within the rigid sleeve 12. Preferably, the rings are LDPE each having an interior surface heat bonded to an exterior surface of flexible conduits. At the radius 15, LDPE rings 17a are integrally formed with the radius 15 with the cross-sectional planes of the rings 17a set at a fixed angle of separation (e.g., about 20 degrees) to support the flexible conduit throughout the 90 degree bend. Again, an interior surface of rings 17a is heat bonded to an exterior surface of the flexible conduit. The rings 17, 17a provide crush resistance. Between the rings 17, 17a, the flexible conduit may flex inwardly and outwardly to better simulate the natural compliance of a natural blood vessel. By way of a further non-limiting example, the discrete rings 17 could be replaced with a continuous helix.

Figure 8:
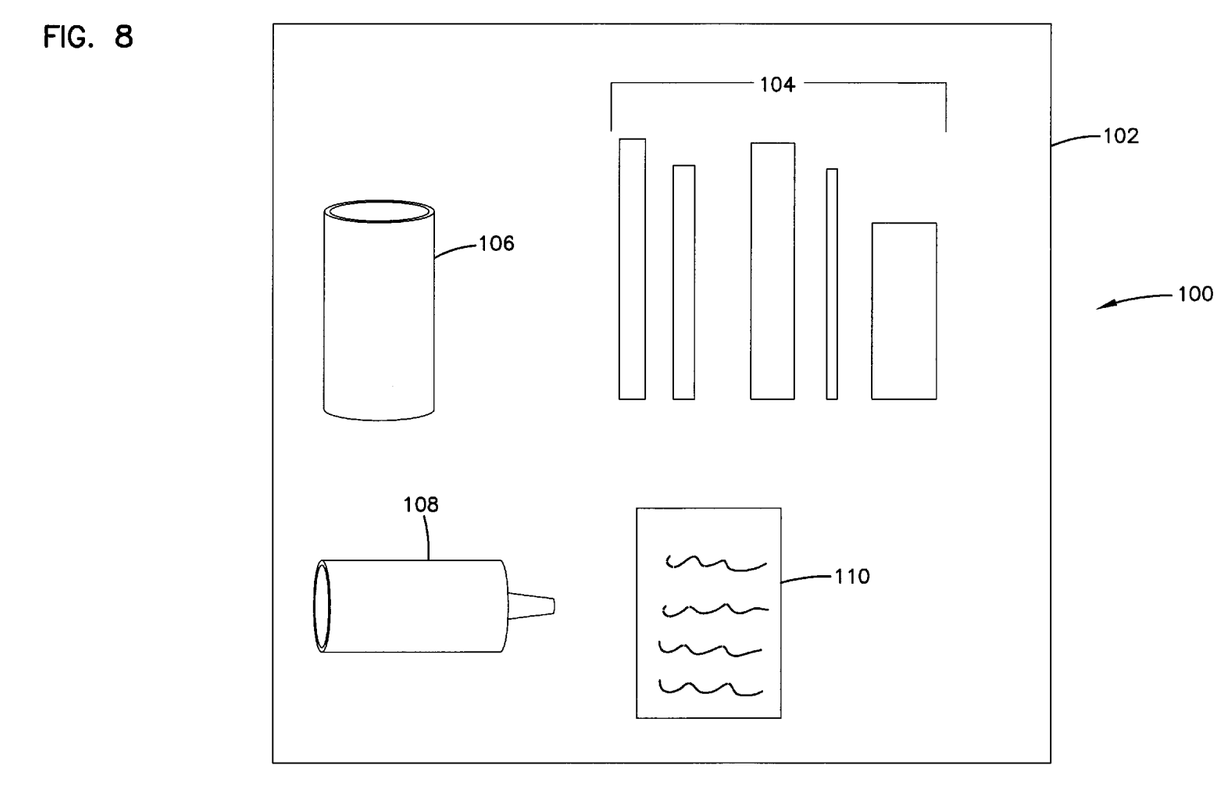
FIG. 8 is a schematic view of a kit according to an embodiment of the present invention.

Referring to FIG. 8, the implant may be provided as part of a sterile, sealed package or kit. An exemplary kit 100 may include a suitable container 102, flexible conduits of varying lengths and inner diameters 104, a housing 106, a securing material 108 such as collagen or another suitable polymer, and instructions 110.

In performing a multi-coronary bypass using an implant according to the present invention, the surgeon is able to tailor the implant to the individual depending on the nature of the procedure and the condition of the individual's heart. The surgeon is capable of selecting the number of flexible conduits as well as the length and inner diameter of each of the flexible conduits. After selecting the number and the inner diameters of each of the flexible conduits, the surgeon assembles the implant. To assemble the implant, the surgeon inserts a first end of each of the conduit into the interior of the housing. Next, the flexible conduits are secured in the housing by injecting a securing material such as collagen or another suitable polymer into the voids between the conduits and allowing the implant to set for a suitable period time. After the implant has been assembled, a first end of the implant housing is inserted into the heart chamber through the heart wall and retained within the heart wall. Then, the second ends of each of the flexible conduits are secured to sites on one or more coronary vessels by an appropriate means.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims are appended hereto.

We claim:

1. An apparatus for performing a multi-vessel coronary bypass procedure comprising:

a housing, the housing having one end configured to extend through a heart wall and into a heart chamber and configured to be sufficiently rigid to withstand a contraction of the heart wall, and a plurality of flexible hollow conduits, each conduit having a first end secured in the housing and a second end configured to be secured to a coronary vessel.

2. The apparatus according to claim 1, further comprising a plurality of reinforcing members secured to an outer surface of each flexible conduit and along a length of each flexible conduit.

3. The apparatus according to claim 1, wherein the hollow conduits have different inner diameters.

4. The apparatus according to claim 1, wherein the first end of each of the flexible conduits is secured in the housing using a securing material that fills voids between the flexible conduits.

5. The apparatus according to claim 1, wherein an inner diameter of each flexible conduit ranges from 1 to 5 mm.

6. A kit for performing a multi-coronary bypass procedure comprising:

a biocompatible sleeve configured to extend through a heart wall;

a plurality of biocompatible conduits configured to be mounted in the sleeve, each conduit having a first end configured to be secured to a coronary vessel;

a securing material for configured to be secure a second end of each flexible conduit in the sleeve; and a container for configured to hold the sleeve, the conduits and the securing material.

7. The kit according to claim 6, wherein each conduit comprises a plurality of reinforcing members secured to an outer surface of the conduit and along a length of the conduit.

8. The kit according to claim 6, wherein the conduits have different inner diameters.

9. The kit according to claim 6, wherein the inner diameter of each conduit ranges from approximately 1 to 5 mm.

10. A method of performing a multi-coronary bypass procedure by using an implant having a sleeve and a plurality of conduits having first end portions that extend through the sleeve and second end portions that project outwardly from the sleeve, the method comprising:

placing the sleeve through a heart wall such that the first end portions of the conduits are placed in fluid communication with a chamber of the heart; and securing the second end portions of the conduits to one or more coronary vessels.

11. The method according to claim 10, wherein the coronary vessels are coronary veins, coronary arteries, or both.

12. The method according to claim 10, wherein the sleeve is sufficiently rigid as to remain open during both systole and diastole.

13. The method according to claim 10, further comprising:

selecting the plurality of conduits such that each conduit has a predetermined inner diameter, and assembling the implant by securing the first end portion of each conduit in the sleeve.

14. The method according to claim 13, wherein each conduit has an inner diameter ranging from approximately 1 to 5 mm.

* * * * *

UNITED STATES PATENT AND TRADEMARK OFFICE
CERTIFICATE OF CORRECTION

PATENT NO. : 6,808,504 B2
DATED : October 26, 2004
INVENTOR(S) : John Schorgl et al.

It is certified that error appears in the above-identified patent and that said Letters Patent is hereby corrected as shown below:

Column 4,
Line 51, "material for configured to be secure" should read -- material configured to secure --.
Line 53, "container for configured" should read -- container configured --.

Signed and Sealed this

Eighth Day of February, 2005

JON W. DUDAS
*Director of the United States Patent and Trademark Office*